United States Patent
Cox

(10) Patent No.: US 6,626,937 B1
(45) Date of Patent: Sep. 30, 2003

(54) AUSTENITIC NITINOL MEDICAL DEVICES

(75) Inventor: Daniel L. Cox, Palo Alto, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 68 days.

(21) Appl. No.: 09/713,708

(22) Filed: Nov. 14, 2000

(51) Int. Cl.$^7$ .................................................. A61F 2/06
(52) U.S. Cl. ...................... 623/1.18; 623/1.19; 623/924; 148/402; 148/563
(58) Field of Search .............................. 623/1.18, 1.19, 623/901, 924; 148/563, 402

(56) References Cited

U.S. PATENT DOCUMENTS

| | | | |
|---|---|---|---|
| 4,425,908 A | | 1/1984 | Simon |
| 4,503,569 A | | 3/1985 | Dotter |
| 4,505,767 A | * | 3/1985 | Quin ........................ 148/402 |
| 4,580,568 A | | 4/1986 | Gianturco |
| 4,665,906 A | | 5/1987 | Jervis |
| 4,856,516 A | | 8/1989 | Hillstead |
| 5,092,877 A | | 3/1992 | Pinchuk |
| 5,292,331 A | | 3/1994 | Boneau |
| 5,350,398 A | | 9/1994 | Pavcnik et al. |
| 5,458,615 A | | 10/1995 | Klemm et al. |
| 5,514,154 A | | 5/1996 | Lau et al. |
| 5,569,295 A | | 10/1996 | Lam |
| 5,643,312 A | | 7/1997 | Fischell et al. |
| 5,766,218 A | | 6/1998 | Arnott |
| 5,885,381 A | | 3/1999 | Mitose et al. |
| 5,907,893 A | | 6/1999 | Zadno-Azizi et al. |
| 6,051,021 A | | 4/2000 | Frid |
| 6,053,992 A | * | 4/2000 | Wu et al. ..................... 148/402 |
| 6,059,810 A | | 5/2000 | Brown et al. |
| 6,068,623 A | | 5/2000 | Zadno-Azizi et al. |
| 6,086,610 A | | 7/2000 | Duerig et al. |
| 6,106,642 A | | 8/2000 | DiCarlo et al. |
| 6,257,513 B1 | * | 7/2001 | Cockerham et al. ........ 242/231 |
| 6,375,458 B1 | * | 4/2002 | Moorlegham et al. .......... 433/2 |
| 6,451,052 B1 | * | 9/2002 | Burmeister et al. ........ 623/1.16 |

OTHER PUBLICATIONS

Pub. No. US 2001/0039446 A1, Pub. Date Nov. 8, 2001, Edwin et al., application 08/833,797.*

Pub. No. US 2001/0039449 A1, Pub. Date Nov. 8, 2001, Johnson et al. application 09/768,700.*

Pub. No. US 2002/0010481 A1, Pub. Date Jan. 24, 2002, Jayaraman et al. application 09/739,830.*

US Pub. No. 2001/0047202 A1, Slaikeu et al., Bioactive aneurysm closure device assembly and kit, filed Jul. 12, 1999.*

(List continued on next page.)

Primary Examiner—Bruce Snow
Assistant Examiner—Cheryl Miller
(74) Attorney, Agent, or Firm—Fulwider Patton Lee & Utecht, LLP

(57) ABSTRACT

A medical device for use within a body lumen that is made from a binary nickel-titanium alloy that remains in its austenitic phase throughout its operational range is disclosed. The medical device, such as an intraluminal stent, is made from superelastic nickel-titanium and may optionally be alloyed with a ternary element. By adding the ternary element and/or through heat treatment, it is possible to lower the phase transformation temperature between the austenitic phase and the martensitic phase of the nickel-titanium alloy. By lowering the phase transformation temperature, the martensite deformation temperature is likewise depressed. It is possible then to depress the martensite deformation temperature below body temperature such that when the device is used in a body lumen for medical treatment, the nickel-titanium device remains completely in the austenitic phase without appearance of stress-induced martensite even if the device is placed under stress.

20 Claims, 2 Drawing Sheets

OTHER PUBLICATIONS

Duerig, T.W. et al., Ti–Ni Shape Memory Alloys, Materials Properties Handbook Titanium Alloys, *Advanced Materials*, 1035–1048, ASM International (1994).

Duerig, T.W. et al., An Engineer's Perspective of Pseudoelasticity, *The Mechanisms of Pseudoelast icit*, 369–393.

Khmelvskaya, I. Y. et al., Thermomechanical Treatment of Ti–Ni Shape Memory Alloys: Transformations, Structure and Properties, *First European Conference on Shape Memory and Superlastic Technologies SMST–99*, 1–8 (Sep. 5–9, 1999).

Nishida, M. et al., Precipitation Processes in Near–Equiatomic TiNi Shape Memory Alloys, *Metallurgical Transactions*, 17A, 1505–1515 (Sep. 1986).

Pelton, A.R. et al., Optimisation of Processing and Properties of Medical Grade Nitinol Wire, *Min Invas Ther & Allied Technol 2000*, 9(1), 107–118.

Simon, M. et al., A Vena Cava Filter Using Thermal Shape Memory Alloy, *Radiology*, 125, 89–94 (Oct. 1977).

\* cited by examiner

AUSTENITIC NITINOL MEDICAL DEVICES

BACKGROUND OF THE INVENTION

The present invention generally relates to medical devices. In particular, the present invention relates to a medical device for use in a body lumen that includes a binary alloy, such as nickel-titanium, that operates exclusively in the austenitic phase.

In the last two decades, binary nickel-titanium (NiTi), or nitinol, alloys have seen an increase in a variety of uses in medical devices. One benefit of applying nitinol to medical devices is that the alloy has tremendous elasticity and shape memory characteristics. Furthermore, as used in medical devices, this material is highly biocompatible, kink resistant, fatigue resistant, and has many other beneficial engineering attributes. One beneficial engineering attribute of nitinol is superelasticity, also commonly referred to as pseudoelasticity. Superelasticity or pseudoelasticity refers to this material's ability to undergo extremely large elastic deformation.

In one particular application, nitinol has found use in self-expanding stents. Historically, stents were not self-expanding but deployed by a balloon. Balloon expanded stents were and are used in conjunction with balloon angioplasty procedures with the intent to reduce the likelihood of restenosis of a vessel. Stents are also used to support a body lumen, tack-up a flap or dissection in a vessel, or in general where the lumen is weak to add support. Examples of intravascular stents can be found in, for example, U.S. Pat. No. 5,292,331 (Boneau); U.S. Pat. No. 4,580,568 (Gianturco); U.S. Pat. No. 4,856,516 (Hillstead); U.S. Pat. No. 5,092,877 (Pinchuk); and U.S. Pat. No. 5,514,154 (Lau et al.).

For balloon expandable stents, the stent is positioned over the balloon portion of the catheter and is expanded from a reduced delivery diameter to an enlarged deployment diameter greater than or equal to the inner diameter of the arterial wall by inflating the balloon. Stents of this type are expanded to an enlarged diameter through deformation of the stent, which then engages the vessel wall. Eventual endothelial growth of the vessel wall covers the stent.

Nitinol then found use in self-expanding stents, where deployment was a result of either shape-memory effect or superelasticity in the material rather than by an inflating balloon. The stent once released from its delivery system assumed a pre-set shape in the body lumen.

Self-expanding stents are used to scaffold the inside circumference of a tubular passage such as an esophagus, bile duct, or blood vessel. Likely the more popular area of application is the cardiovascular system, where a self-expanding stent is used subsequent to balloon angioplasty. Cardiovascular stents currently available in the United States are made of stainless steel, and are expanded against the vessel wall by plastic deformation caused by the inflation of a balloon placed inside the stent. Nitinol stents, by comparison, are self-expanding. Instead of being deformed to the vessel diameter by a balloon catheter, the nitinol stent returns to its non-deformed, equilibrium shape. Examples of stents made of a superelastic nitinol alloy are disclosed in U.S. Pat. No. 4,503,569 (Dotter); and U.S. Pat. No. 4,665,906 (Jervis).

The benefits of using a superelastic nitinol material for self-expanding stents are primarily related to its large recoverable strain. The biocompatability of nickel-titanium is also an attractive benefit for use of this material in stenting applications, because the stent remains in the patient as part of the treatment.

The use of nickel-titanium as a balloon-expandable stent is less common. At present, the PARAGON Stent is a balloon-expandable nickel-titanium stent. The balloon-expandable and scaffolding capabilities of the PARAGON Stent are accomplished by setting the austenite finish temperature ($A_f$) at about 55 degrees C. or well above body temperature. The stent is therefore completely martensitic before, during, and after balloon deployment. A significant disadvantage of such a balloon-expandable nitinol stent in its martensitic phase is that martensite is very soft. Therefore, the scaffolding function and hoop strength of the stent are diminished.

As briefly described above, superelasticity or pseudoelasticity, refers to the highly exaggerated elasticity or spring-back observed in many nickel-titanium alloys deformed above its austenite start temperature ($A_s$) and below the martensite deformation temperature ($M_d$). Hence, nickel-titanium alloys can deliver over fifteen times the elastic motion of a spring steel. The martensite deformation temperature ($M_d$) is defined as the temperature above which martensite cannot be stress-induced. Consequently, nickel-titanium remains in its austenitic phase throughout an entire tensile test above $M_d$.

The evolution of superelastic and shape memory alloy stents has progressed to the use of ternary elements in combination with nickel-titanium alloys to obtain specific material properties. Use of a ternary element in a superelastic stent is shown in, for example, U.S. Pat. No. 5,907,893 (Zadno-Azizi et al.). As a general proposition, there have been attempts at adding a ternary element to nickel-titanium alloys as disclosed in, for instance, U.S. Pat. No. 5,885,381 (Mitose et al.).

Nitinol alloys contain more nickel than does 316L-grade stainless steel, the most common material used for medical devices. It is recognized that nickel is considered toxic. As nitinol oxidizes, it forms a titanium oxide layer ($TiO_2$), with small islands of pure nickel on the surface, or, depending on the treatment, with no nickel present at the surface. Accordingly, nitinol is highly biocompatible and more so than stainless steel.

Nitinol has found its way into other medical device applications. An example of a guide wire made of superelastic nitinol for performing angioplasty or vascular intervention procedures is disclosed in U.S. Pat. No. 6,068,623 (Zadno-Azizi et al.).

Still other medical device applications for nitinol include filters. Pulmonary embolism is the sudden obstruction of a blood vessel by blood emboli, the emboli typically formed in the veins of the pelvis and lower extremities of a person's body. Because migration of the blood emboli to the pulmonary artery can interrupt the oxygenization process of the lungs, the disease has a high mortality rate. Vena cava filters have been developed as one method for preventing pulmonary embolism. Such a device is disclosed in U.S. Pat. No. 5,350,398 (Pavcnik et al.) Nitinol has been used in fabricating vena cava filters. One discussion of such a use can be found in "A Vena Cava Filter Using Shape Memory Alloy," M. Simon, R. Kaplow, E. Salzman, D. Freiman, Radiology, Vol. 125, pp. 89–94, October 1997. According to the authors, their vena cava filter uses shape memory to deploy into its pre-set, austenitic shape, where the reversion to the pre-set, austenitic shape is triggered by application of heat.

In view of the foregoing, there is still a need for a medical device that operates exclusively in the austenitic range. Such a device is further compatible with balloon catheters. If fabricated into a stent, such a device would have great radial hoop strength. With all of these benefits, the austenitic medical device would also be highly biocompatible, have greater MRI compatibility, and would be more flexible than medical grade stainless steel.

SUMMARY OF THE INVENTION

The present invention is directed to a medical device for use in a lumen of a mammalian body, comprising an intraluminal element wherein the element includes a binary pseudoelastic alloy, and the pseudoelastic alloy includes a martensitic phase and an austenitic phase with a phase transformation temperature set below the mammalian body temperature such that the pseudoelastic alloy of the intraluminal element is always in the austenitic phase within the mammalian body. In a preferred embodiment, the mammalian body is the human body where the body temperature is below 37 degrees C. Furthermore, the binary pseudoelastic alloy is preferably nickel-titanium, but may optionally include a ternary element. Furthermore, the pseudoelastic alloy has an austenite start temperature ($A_s$), an austenite finish temperature ($A_f$), and a martensite deformation temperature ($M_d$) that is 25 degrees to 50 degrees C. or more above the austenite finish temperature ($A_f$).

In an alternative embodiment, the present invention is directed to a medical device for use in a lumen of a human body comprising an intraluminal element, wherein the element includes a binary pseudoelastic alloy, and the pseudoelastic alloy has a martensitic phase and an austenitic phase, wherein a martensite deformation temperature ($M_d$) of the alloy is depressed below human body temperature.

In order to achieve complete austenitic state throughout the operating range of the medical device, and without having appearance of pseudoelasticity, it is desirable to set the transformation temperature of the alloy well below body temperature. That is, $M_d$ is set below 37 degrees C. In this situation, it would no longer be possible to stress-induce martensite in the device at body temperature.

The lowering of the transformation temperature could be achieved by adding nickel or other commonly known nickel-titanium additives. It is also possible to heat treat the nickel titanium alloy to achieve the depressed transformation temperature.

The resulting nickel-titanium alloy of the present invention can be used in a medical device such as a stent for intravascular implantation where the stent is balloon-expandable. Conventional nitinol stents suffer from recoil and cannot be balloon-expandable. Furthermore, if the stent becomes martensitic, the radial hoop strength is weakened. In comparison, the present invention austenitic only stent does not suffer from these disadvantages. Furthermore, austenite has three times the modulus of elasticity of martensite, and as such, is a much stronger material to perform its scaffolding function.

DETAILED DESCRIPTION OF THE PREFERRED EMBODIMENTS

The present invention is directed to an austenitic medical device made of preferably a binary alloy such as nickel-titanium or nitinol. By way of illustration, the following exemplary embodiments are limited to intraluminal stents. However, it is recognized that the present invention is not limited to such applications but also contemplates use in various other medical devices including, for example, guide wires, vena cava filters, surgical staples, aneurysm clips, bone screws, etc. where the same principles apply.

Figure 1:
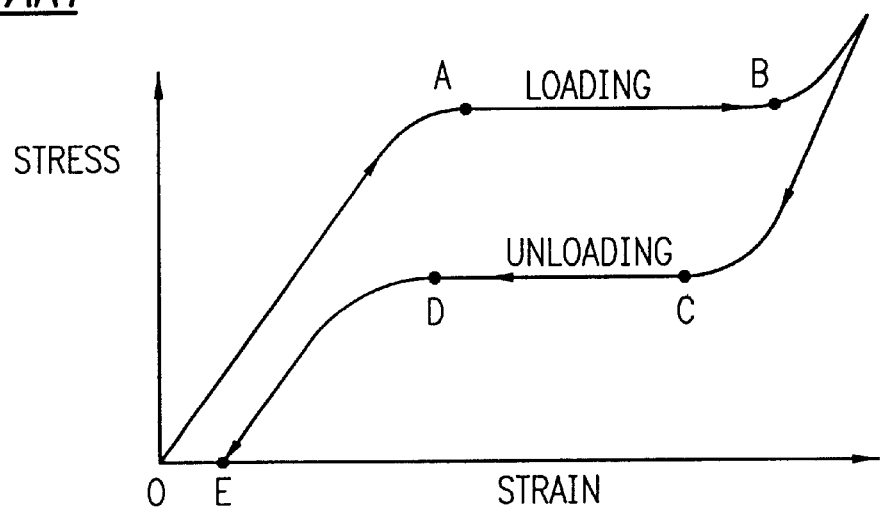
FIG. 1 is an idealized stress-strain curve for a nickel-titanium superelastic alloy.

FIG. 1 is a commonly understood stress-strain curve for a binary nickel-titanium alloy showing loading and unloading of the metal alloy. Industry literature provide more detailed discussions of nickel-titanium behavior. An example of such includes T. W. Duerig, A R. Pelton, "Ti—Ni Shape Memory Alloys, Materials Properties Handbook Titanium Alloys," pp. 1035–1048, ASM International (1994), the contents of which are incorporated by reference. The curve illustrated in FIG. 1 is also generally known as a superelastic curve, characterized by regions of nearly constant stress during loading and unloading, so labeled on the curve. Constant loading stress represented by line segment A–B is referred to as the loading plateau stress, and constant unloading stress represented by line segment C–D is referred to as the unloading plateau stress. The distance between E and the origin O of FIG. 1 represents the "amnesia" or permanent set of the material where the strain is not recoverable.

Accordingly, FIG. 1 represents an idealized stress-strain hysteresis curve for a nickel-titanium alloy tested above its austenite finish temperature ($A_f$) but below its martensite deformation temperature ($M_d$). As is known in the art, the austenite finish temperature ($A_f$) is the temperature at which the nickel-titanium material completely converts to austenite, and the narrow temperature range just above $A_f$ is where the onset of superelasticity occurs. Importantly, superelasticity performance steadily deteriorates until the martensite deformation temperature ($M_d$), at which point stress-induced martensite no longer appears, and all superelasticity is eliminated.

However, the curve illustrated in FIG. 1 represents the temperature range just above $A_f$ in which superelasticity does occur. In this instance, as the material is stressed, the curve is represented by sloped line O–A in which the material is entirely austenitic. At knee generally labeled point A is the transformation from austenite to stress-induced martensite (SIM). At a certain theoretical stress level, maintaining constant stress completely converts the austenite to stress-induced martensite in the nickel-titanium alloy, as represented by line segment A–B. Segment A–B is also known as the loading plateau stress. Beyond point B, further application of stress creates elastic deformation in the stress-induced martensite. Continued application of stress leads to elastic deformation (the upward slope) then plastic deformation (not shown) in the stress-induced martensite.

Release of stress causes the curve in FIG. 1 to reverse its slope beyond point B, dropping down to point C. Generally, at or about point C represents the initial conversion of stress-induced martensite back to austenite. At a certain constant stress plateau, represented by line segment C–D, the material converts entirely from the stress-induced martensitic phase to the austenitic phase. Further lowering of the applied stress is represented by sloped line D–E in which the elastic deformation of the austenitic phase is represented. As mentioned above, strain E is the permanent set of unrecoverable strain in the material.

Figure 2:
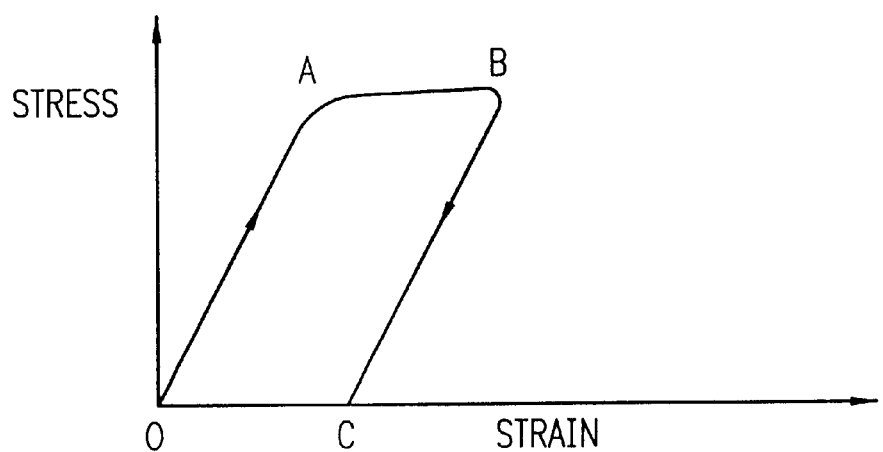
FIG. 2 is an idealized stress-strain curve for the alloy used in the present invention austenitic medical device.

FIG. 2 is an idealized stress-strain hysteresis curve for a nickel-titanium alloy in which the stress is applied at a temperature above the martensite deformation temperature ($M_d$). In such case, there is never an appearance of stress-induced martensite, and accordingly the curve of FIG. 2 represents the austenitic phase only. One way to achieve such a performance curve is to depress the $M_d$ temperature below the body temperature of the patient so that the operation of the medical device is always at a temperature above the $M_d$ temperature, ensuring that the alloy remains entirely austenite while inside the patient.

That is, the transformation temperature between the martensitic phase and the austenitic phase is set below body temperature so that when the medical device is implanted in the body lumen, it is entirely in the austenitic state. The transformation temperature can loosely refer to $A_s$, $A_f$, $M_s$, $M_f$, or $M_d$. It is preferable to work with the martensite deformation temperature $M_d$. For the exemplary embodiment, the $A_s$ or $A_f$ is depressed to a range of −150 to −100 degrees C. With the $M_d$ temperature depressed well below body temperature, stress-induced martensite cannot appear despite application of stress while the device is in the body. Contrast this behavior to the superelastic curve shown in FIG. 1 where application of stress creates stress-induced martensite in the material, as represented by the flat plateau stresses.

Thus, in FIG. 2, if stress is applied to such an alloy, the curve is represented by the increasing slope O–A. Segment O–A represents the elastic deformation of the material. Continued application of stress results creates a slight knee at point A but with proportional increase in strain relative to stress in segment A–B. Along segment A–B, or anywhere else son the curve, there is no phase transformation and no appearance of stress-induced martensite (SIM). Further application of stress beyond point B (not shown) results in plastic deformation and failure of the material. As stress is released, the curve represented by segment B–C shows a relatively linear release of stress proportional to recovery of strain. The distance between point C and O is the permanent set of the material as a result of the applied stress. In some cases, if stress is low, there is no permanent set and recovery is back to the origin O.

Accordingly, the material illustrated in FIG. 2 is applied to a medical device for use in a mammalian body such as a human body. In other words, the present invention applies the aforementioned FIG. 2 nitinol alloy to various medical device applications.

Figure 3:
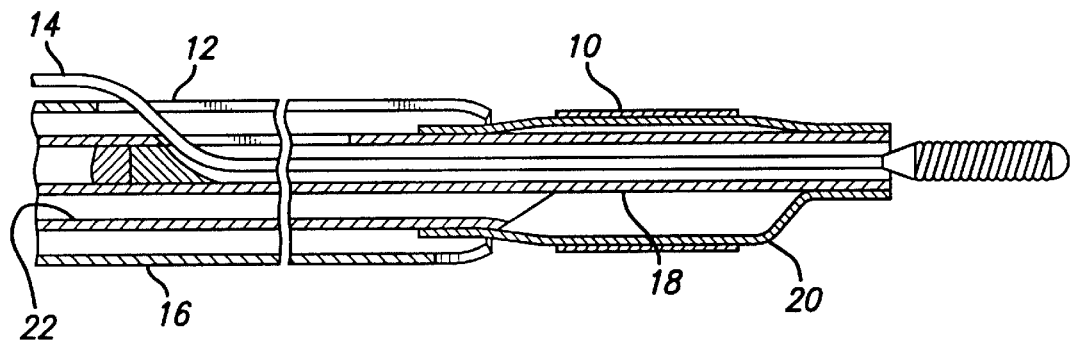
FIG. 3 is a cross-sectional view of a delivery system for delivering an exemplary embodiment stent of the present invention to a lesion within a body lumen.

In one exemplary application, the nitinol alloy is used to fabricate a stent. FIG. 3 is a cross-sectional drawing of a rapid exchange stent delivery system showing only the distal end of the system and part of the rapid exchange area. This delivery system is just one example of a delivery system that can be used with the present invention. More details of this type of delivery system may be found in U.S. Pat. No. 5,458,615 (Klemm et al.), entitled "Stent Delivery System." Other delivery systems, such as well known over-the-wire delivery systems may be used without departing from the scope of the present invention. In FIG. 3, the delivery system includes an expandable balloon 20 supporting an austenitic stent 10 made in accordance with the present invention. An inflation lumen 22 is used to inflate and deflate the balloon 20 to deploy the present invention austenitic stent 10 at the lesion.

Figure 4:
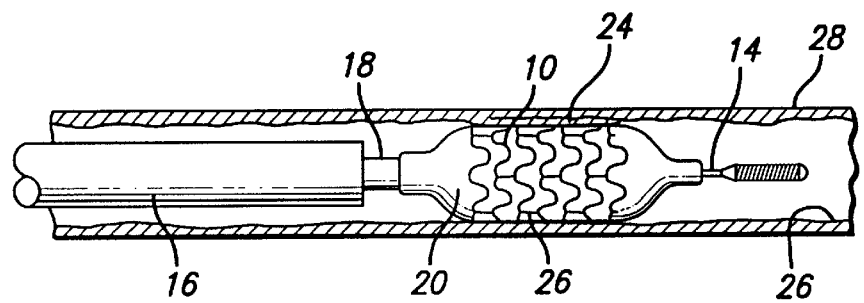
FIG. 4 is a side elevational view showing deployment of the austenitic stent from FIG. 3.

FIG. 4 represents the present invention medical device positioned at a lesion 24 within a body lumen 28. The various procedures for locating and deploying a stent within a body lumen is well known in the art. Generally, the guide wire 14 is used to select the vessel and is followed by the delivery system to locate the stent 10 at the lesion 24. The lesion, in this case, is a flap which if left untreated may cause a stenosis or restenosis. As shown in FIG. 4, the delivery sheath is withdrawn to expose the stent 10 on the balloon 20. The balloon 20 is then expanded to deploy the austenitic stent 10 against the vessel wall 26. Because the stent 10 is in the austenitic phase, in spite of the applied stress of the inflating balloon 20, the stent 10 exhibits superior hoop strength and has minimal recoil.

Indeed, the austenitic stent 10 is formed from a superelastic material such as nickel-titanium and at the ambient temperature, for example body temperature of a human, it is in its austenitic phase. Because the martensite deformation temperature ($M_d$) has been depressed, any stress such as application of expansion pressure by the balloon 20 does not create stress-induced martensite in the stent 10 in the conditions shown in FIG. 4.

In FIG. 3, the stent 10 is maintained in its smaller delivery diameter prior to deployment. It remains in its austenitic phase at room temperature and while positioned inside a body lumen. This is accomplished by setting the transition temperature below room temperature to insure that the nitinol stent 10 remains austenitic, and by depressing the martensite deformation temperature ($M_d$), deployment of the stent 10 does not generate stress-induced martensite. Thus, the behavior of the stent 10 is not superelastic.

In certain instances, however, there could be some stress-induced martensite at room temperature. If, for example, $M_d$ is set higher than room temperature but lower than the patient's body temperature ($T_{room}<M_d<T_{body}$), stress-induced-martensite might appear in the stent 10.

Inflation of the balloon 22 deforms the austenitic stent 10 to the proper deployment diameter. Thereafter, the balloon 22 is deflated and the delivery system is withdrawn leaving the deformed austenitic stent 10 at the lesion 24. The austenitic stent 10 possesses great hoop strength so it easily embeds in the vessel wall 26 during deployment. Furthermore, the great hoop strength is valuable to the austenitic stent 10 in performing its scaffolding function. Once embedded, the austenitic stent 10 exhibits minimal recoil so it remains embedded and cannot migrate downstream.

Figure 5:
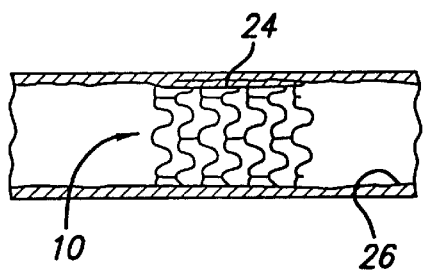
FIG. 5 is a side elevational view of the present invention austenitic stent deployed at a lesion.

The present invention austenitic stent 10 is fabricated by various processes such as that disclosed in U.S. Pat. No. 5,569,295 (Lam), entitled "Expandable Stents And Method For Making Same," the contents of which are incorporated by reference. Generally speaking, the present invention austenitic stent is preferably laser cut from a tube with various heat treating and finishing processes involved. It is important to note that the strut pattern shown in FIGS. 4 and 5 are only exemplary and not to be limiting. The present invention is easily adaptable to numerous strut patterns.

To ensure the stent remains in the austenitic state throughout delivery and deployment within a body lumen, it is necessary to set the phase transformation temperature of the binary alloy below the body temperature of the person or mammal. Furthermore, it is desirable to depress the martensite deformation temperature ($M_d$) below body temperature such that even if the stent encountered stress, there would be no reversion of the alloy to its stress-induced martensitic phase. Typically, the $M_d$ temperature is 25 degrees to 50 degrees C.—and in some instances as much as 100 to 150 degrees C.—above the $A_f$ temperature. Therefore, by depressing $A_f$ to well below body temperature of a human of 37 degrees C., the $M_d$ temperature would be set well below the 37 degree C. temperature as well.

Various methods are possible to depress the austenite finish temperature in order to depress the martensite deformation temperature. One method is to substitute an element such as iron (Fe), aluminum (Al), chromium (Cr), cobalt (Co), or vanadium (V) for the nickel in the binary nickel-titanium alloy to depress $M_s$. For example, by alloying binary nickel-titanium with 3 atomic percent iron (Fe) or 5 atomic percent vanadium (V), the $A_f$ of the alloy can be depressed. Any one or combination of these alloying elements tend to lower the transformation temperature yet improve the strength of the stent.

Another method for depressing $A_f$ is to use binary nickel-titanium with an increased nickel content in the, for example, 51 to 52 atomic percent range.

It is also possible to depress the transformation temperature and likewise the martensite deformation temperature by heat treating. For example, using high temperature thermomechanical treatment of the nitinol stent is one possibility. This process involves hot plastic deformation of a stable austenite followed by quench cooling. High temperature thermomechanical treatment of the austenite leads to a noticeably lowered martensitic transformation temperature range and more importantly, a lowered $A_s$. For example, for a Ni—Ti—Fe alloy at 47 atomic percent nickel and 3 atomic percent iron, by hot working at deformation temperatures of approximately 500 to 1000 degrees C. with water quench, the $A_s$ tends to be depressed. A general discussion of the foregoing can be found in, for example, I.Khmelevskaya, S.Prokoshkin, *"Thermomechanical Treatment of Ti—Ni Shape Memory Alloys: Transformations, Structure and Properties,"* First European Conference on Shape Memory and Superelastic Technologies SMST-99, pp. 1–8 (Sep. 5–9, 1999, Antwerp, Belgium), whose entire contents are hereby incorporated by reference.

While the present invention has been illustrated and described herein in terms of a superelastic stent wherein the stent assumes only an austenitic phase throughout its operational range inside a body lumen, it is apparent to those skilled in the art that the present invention can be used in other instances. Other modifications and improvements may be made without departing from the scope of the present invention.

What is claimed is:

1. A medical device for use in a mammalian body, comprising:
   a structurally expandable intraluminal element, wherein the intraluminal element includes a binary superelastic alloy; and
   the superelastic alloy includes a martensitic phase and an austenitic phase, with a transformation temperature set below a mammalian body temperature such that the superelastic alloy of the intraluminal element is always in the austenitic phase with no stress-induced martensite while under applied stress within the mammalian body.

2. The medical device of claim 1, wherein the binary superelastic alloy includes nickel-titanium.

3. The medical device of claim 1, wherein the mammalian body temperature is at most 37 degrees C.

4. The medical device of claim 1, wherein the binary superelastic alloy includes a ternary element selected from the group of elements consisting of: chromium (Cr), cobalt (Co), vanadium (V), or iron (Fe).

5. The medical device of claim 1, wherein the binary superelastic alloy includes titanium and a second element selected from the group of elements consisting of: iron (Fe), aluminum (Al), chromium (Cr), cobalt (Co), or vanadium (V).

6. The medical device of claim 1, wherein the binary superelastic alloy exhibits no superelastic behavior within the mammalian body.

7. The medical device of claim 1, wherein the transformation temperature includes at least one of an austenite start temperature ($A_s$) and an austenite finish temperature ($A_f$) that is 25 to 150 degrees C. below a martensite deformation temperature ($M_d$).

8. A medical device for use in a lumen of a human body, comprising:
   an intraluminal element, wherein the element includes a binary superelastic alloy; and
   the superelastic alloy having a martensitic phase and an austenitic phase, wherein a martensite deformation temperature ($M_d$) of the alloy is depressed to below human body temperature.

9. The medical device of claim 8, wherein the binary superelastic alloy includes nickel-titanium.

10. The medical device of claim 8, wherein the superelastic alloy includes hot working to depress the martensite deformation temperature ($M_d$) of the alloy.

11. The medical device of claim 8, wherein the binary superelastic alloy includes a ternary element.

12. The medical device of claim 8, wherein the superelastic alloy does not include stress-induced martensite.

13. The medical device of claim 8, wherein the superelastic alloy is defined by at least one of an austenite start temperature ($A_s$) and an austenite finish temperature ($A_f$) that is 25 to 150 degrees C. below the martensite deformation temperature ($M_d$).

14. A method for providing a medical device for use in a lumen of a human body, comprising:
   providing an intraluminal element having a binary superelastic alloy, wherein the superelastic alloy includes a martensitic phase and an austenitic phase; and
   depressing a martensite deformation temperature ($M_d$) of the alloy to below human body temperature.

15. The method of providing a medical device of claim 14, wherein the binary superelastic alloy includes nickel-titanium.

16. The method of providing a medical device of claim 14, wherein the method in includes hot working and quenching the alloy to depress a transformation temperature thereof.

17. The method of providing a medical device of claim 14, wherein the method includes adding a ternary element to depress the martensite deformation temperature ($M_d$).

18. The method of providing a medical device of claim 14, wherein the method includes heat treating the alloy to depress the martensite deformation temperature ($M_d$).

19. The method of providing a medical device of claim 14, wherein the superelastic alloy does not include stress-induced martensite.

20. The method of providing a medical device of claim 14, wherein a stress-strain hysteresis curve of the alloy has no flat plateaus.

* * * * *

UNITED STATES PATENT AND TRADEMARK OFFICE
CERTIFICATE OF CORRECTION

PATENT NO.   : 6,626,937 B1  
DATED        : September 30, 2003  
INVENTOR(S)  : Daniel L. Cox It is certified that error appears in the above-identified patent and that said Letters Patent is hereby corrected as shown below:

<u>Column 7,</u>  
Lines 48, 55, 58 and 62, change "mammalian", to read -- human --.  
Line 65, before "includes", add -- further --.

<u>Column 8,</u>  
Replace lines 16 and 17, to read -- A medical device comprising: an intraluminal element for use in a lumen of a human --.  
Line 22, delete "depressed".  
Line 30, before "includes", add -- further --.

Signed and Sealed this

Second Day of March, 2004

JON W. DUDAS  
*Acting Director of the United States Patent and Trademark Office*